United States Patent [19]

Fujiwara et al.

[11] 4,220,716

[45] Sep. 2, 1980

[54] PROCESS FOR THE PREPARATION OF 7α-HYDROXYLATED STEROIDS

[75] Inventors: Mitsuhiko Fujiwara; Akiko Fujiwara, both of Kamakura; Chikara Miyamoto, Yokohama, all of Japan

[73] Assignee: Hoffmann-La Roche Inc., Nutley, N.J.

[21] Appl. No.: 939,613

[22] Filed: Sep. 5, 1978

[30] Foreign Application Priority Data

Sep. 2, 1977 [CH] Switzerland ............... 10733/77

[51] Int. Cl.$^2$ ............................................. C12P 33/06
[52] U.S. Cl. ..................................... 435/58; 435/931
[58] Field of Search ........................ 195/51 S; 435/58

[56] References Cited

U.S. PATENT DOCUMENTS

| | | | |
|---|---|---|---|
| 2,924,611 | 2/1960 | Dodson et al. | 195/51 S |
| 2,960,436 | 11/1960 | Thoma et al. | 435/58 |
| 2,962,512 | 11/1960 | Bernstein et al. | 435/58 |
| 3,031,477 | 4/1962 | Thoma et al. | 435/58 |

FOREIGN PATENT DOCUMENTS

1101413 9/1961 Fed. Rep. of Germany .

OTHER PUBLICATIONS

Charney et al., Microbial Transformations of Steroids, pp. 286, 382, 383, 396, 397, 449 and 586 (1967).
Chem. Abst. 62, 7823g (1965).
J. Org. Chem. 24 286 to 289 (1959).
J. Org. Chem. 26 2856 to 2859 (1961).
Canadian J. Microbiol. 13 1271 to 1281 (1971).
Canonica et al, Gazzetta Chimica Italiana, vol. 93, pp. 301–308 (1963).

*Primary Examiner*—Alvin E. Tanenholtz
*Attorney, Agent, or Firm*—Jon S. Saxe; George M. Gould; James H. Callwood

[57] ABSTRACT

A fermentation process for the preparation of 7α-hydroxylated steroids utilizing strains of the genus Mucor is disclosed. The 7α-hydroxylated steroids are useful intermediates for the synthesis of chenodeoxycholic acid as well as steroidal hormones.

5 Claims, No Drawings

PROCESS FOR THE PREPARATION OF 7α-HYDROXYLATED STEROIDS

DESCRIPTION OF THE INVENTION

The present invention relates to a process for the preparation of 7α-hydroxylated steroids by fermenting 7-unsubstituted steroids of the pregnene or androstene series with microorganisms of the genus Mucor.

The microbiological preparation of 7α-hydroxylated steroids by means of microorganisms of the genera Cephalosporium, Helminthosporium, Curvularia, Rhizopus, Aspergillus, Diplodia and Cunninghamella has been described. However, the selective introduction of a hydroxy group in the 7α-position of steroids of the following formula I by means of microorganisms of the genus Mucor has not been described.

The process in accordance with the present invention is characterized in that a compound of the general formula

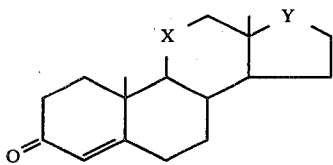

wherein X is —CH$_2$—,

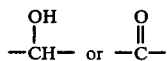

and Y is a radical of the formula

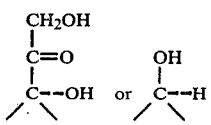

is fermented with a microorganism of the genus Mucor. The process in accordance with the invention yields compounds of the formula

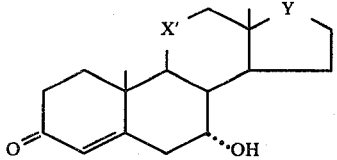

wherein X' is —CH$_2$— or

and Y is as above.

In accordance with the invention there can be used all strains of the genus Mucor which are capable of 7α-hydroxylating a 7-unsubstituted steroid of the formula I. Preferred strains are Mucor spinescens IAM-6071 (FERM P-No. 4141), *Mucor circinelloides* ETH-2605 (FERM P-No. 4142), *Mucor hiemalis* IFO-8448 (FERM P-No. 4143), and IFO-8449 (FERM P-No. 4144), *Mucor plumbeus* CBS 295.63, *Mucor hiemalis* FERM P-No. 3800 and variants thereof.

The notation FERM P- relates to cultures of the Fermentation Research Institute, Chiba City, Japan (FRI); IAM denotes the Institute of Applied Microbiology, University of Tokyo, IFO denotes the Institute for Fermentation, Osaka, Japan, CBS denotes the Centraalburea voor Schimmelcultures in Baarn, Netherlands; and ETH denotes the Eidgenössische Technische Hochschule Zurich, Switzerland.

The microorganisms can be used in the form of the culture broth, the mycelium or in processed form. The culture broth can be prepared by inoculating a suitable medium with the microorganism. The culture medium can contain carbon sources, nitrogen sources, inorganic salts and other nutrient substances suitable for the growth of the microorganism. As carbon sources there may be mentioned, for example, glucose, sucrose, dextrin, mannose, starch, lactose and glycerine. As nitrogen sources there may be mentioned, for example, nitrogen containing organic substances such as peptone, meat extract, yeast extract, cornsteep liquor and casein or nitrogen-containing inorganic compounds such as nitrates and inorganic ammonium salts. As inorganic salts there may be mentioned phosphates or sodium, potassium, magnesium, manganese, iron and copper salts.

The cultivation of the microorganism can be carried out as a submersed culture, as a shaking culture or as a stationary culture. The microorganism is preferably cultivated under aerobic conditions.

The process provided by the invention is conveniently carried out by adding the 7-unsubstituted steroid of formula I to be 7α-hydroxylated as the substrate to the cultivated culture broth. The concentration of the substrate conveniently amounts to about 0.1 to about 20 g/l. The 7α-hydroxylation can be carried out by continuing the cultivation of the microorganism under the above-mentioned conditions. The cultivation time can be varied depending on species and strain of microorganism used, on the composition of the culture medium and on substrate used and its concentration. In general, a fermentation time of 1 to 10 days is sufficient. The cultivation is generally performed between about 20° and about 30° C. and at a pH of about 4 to about 9.

The substrate can be added to the culture of the microorganism during the cultivation or to the culture medium before the sterilization or the inoculation.

The 7α-hydroxylation of the invention can be carried out with the mycelium of the microorganism isolated from the culture solution or with an enzyme extract prepared by methods known in the art from the culture broth or the mycelium. In this case, the 7α-hydroxylation can be carried out conveniently in solution, for example, a buffer solution, in physiological salt solution, in fresh nutrient solution or in water.

The 7-unsubstituted starting material or formula I can be added as a fine powder or as a solution in a hydrophilic solvent such as acetone, dimethyl sulphoxide, methanol, ethanol, ethyleneglycol, propyleneglycol or dioxane. Alternatively, a surfactant or a dispersion agent to an aqueous suspension of the substrate or the substrate can be emulsified by ultrasonic treatment.

Examples of 7-unsubstituted steriod starting materials of formula I are 17α,21-dihydroxy-4-pregnene-3,20-dione, 11β,17α,21-trihydroxy-4-pregnene-3,20-dione, 17α,21-dihydroxy-4-pregnene-3,11,20-trione and 17β-hydroxy-4-androsten-3-one. From these 7-unsubstituted steroids there are obtained the corresponding 7α-hydroxy derivatives. When 11β,17α,21-trihydroxy-4-pregnene-3,20-dione is used, the 11-hydroxy group is simultaneously oxidized to the carbonyl function.

The fermentation product can be isolated from the fermentation mixture by methods known in the art, for example, by solvent extraction with a water immiscible organic solvent, such as chloroform, methylene chloride or ethyl acetate or by chromatography on an absorbent such as aluminum oxide, silica gel or cellulose. The fermentation product can be purified by recrystallization from solvents such as, for example, ethyl acetate, benzene or acetone.

The 7α-hydroxy steroids of formula II of the present invention are useful as intermediates for the synthesis of hormones, chenodeoxycholic acid and other pharmaceuticals.

The characteristic mycological features of *Mucor hiemalis* NRRL 11093 (FERM-P No. 3800) are as follows:

I. Growth

Colonies on malt extract agar and potato-dextrose agar, growing very rapidly reach 9 cm in diameter and up to 1.5 cm in height within 3 to 5 days at about 25° C. They are pale grey to pale olive grey, and floccose in appearance. Dense substrate mycelium is distinctive brilliant yellow on synthetic-mucor agar.

Germination occurs only slightly at about 37° C. but growth is never observed macroscopically; good growth and sporulation at about 5° to about 30° C., though slow at lower temperatures. Optimum temperature for its growth is about 20° to about 27° C. and optimum pH is between about 4.0 and about 8.0.

II. Morphology

Sporangiophores are up to 15μ in diameter, slightly branched sympodially, with or without yellowish contents; branches are often slightly swollen and roughened at the base. Sporangia are 23.4–80.4 (−130)μ in diameter, globose, and dark brown to almost black, with deliquescent walls that leave small collarettes.

Columellae are 19.2–41.8×13.4–36.7μ, mostly ellipscidal or obovoidal, but globose or pyriform ones are also seen. Sporangiospores are variable in size and shape, 5.0–16.7×3.3–8.4μ, smooth-walled and colorless though olive to olive brown in mass.

Zygospores are obtained in matings with a minus strain of Mucor hiemalis IFO-8449 on potato-dextrose agar at about 20° C.; they are 36.7–80.0μ in diameter, globose or nearly so, brown to almost black and roughened with spines. Suspensors are uniform in size, unappendaged, tinged yellow brown and often delicately roughened. Zygospore formation is not observed at about 25° C. or higher.

Morphological features of the strain FERM-P No. 3800, globose sporangia, presence of distinct columellae, and absence of apophyse, stolon and rhizoids, are the characteristics of the genus Mucor described by J. A. von Arx in "The Genera of Fungi Sporulating in Pure Culture", 2nd edition, pp. 35–49, (A. R. Gantner Verlag, 1974). This well-known and large genus is divided into 7 sections, of which the features of Section Hiemalis show quite close morphological similarities to those of the strain FERM-P No. 3800 in terms of pale grey to pale olive grey colony, less than 2 cm in height, sympodially branched sporangiophores and brownish to blackish globose sporangia, not over 100μ in diameter with deliquescing walls as described in Mucorales, pp. 2–48, 1969, by H. Zycha et al.

According to the classification of those belonging to Section Hiemalis by M. A. A. Schipper ("A Study on Variability in Mucor hiemalis and Related Species" in Studies in Mycology, 1973, No. 4. pp. 1–40) the strain FERM-P No. 3800 belongs to Mucor hiemalis f. hiemalis which was confirmed by the formation of zygospores with a minus strain of Mucor hiemalis IFO-8449.

Thus the present strain was identified as *Mucor hiemalis* wehmer f. hiemalis.

Morphological features of Mucor spinescens IAM-6071 (FERM P-No. 4141) and Mucor circinelloides ETH-2605 (FERM P-No. 4142) coincide almost with those described in M. A. A. Schipper ("A Study on Variability in Mucor spinescens and Mucor circinelloides, and Related Species") in Studies in Mycology, No. 12, March 15, 1976.

The following Examples illustrate the present invention:

EXAMPLE 1

A fermentation medium containing 1% cornsteep liquor and 1% glucose was prepared and adjusted to pH 6.5 prior to the sterilisation. 100 ml portions of this medium were distributed into 20 500 ml Erlenmeyer flasks, the flasks were plugged with paper stoppers and sterilised at 120° C. for 15 minutes. After cooling, the flasks were inoculated with the mycelium of a 2 week old agar culture of Mucor hiemalis FERM-P-3800.

The flasks were then shaken at 26.5° C. on a shaking machine with 180 strokes/minute. After 24 hours, 50 mg of 17α, 21-dihydroxy-4-pregnene-3,20-dione in 1 ml of dimethyl sulphoxide were added to each flask. The incubation was continued for 69 hours. Thereafter, the culture was harvested, filtered and washed with water. The filtrate and washings were combined and extracted twice with 2 liters of ethyl acetate. After drying over sodium sulphate, the extracts were concentrated under reduced pressure to a small volume of oily substance. The concentrate was chromatographed on a silicic acid (Mallinkcrodt) column using chloroform/acetone for the elution. The 7α,17α,21-trihydroxy-4-pregnene-3,20-dione was eluted with chloroform-acetone (7:3). The homogeneous fractions were concentrated and recrystallised from ethyl acetate to yield 196 mg of 7α,17α,21-trihydroxy-4-pregnene-3,20-dione of melting point 221.5°–223.5° C.

EXAMPLE 2

In a manner analogous to that described in Example 1, individual flasks were fermented with Mucor spinescens IAM-6071, *Mucor circinelloides* ETH-2605, *Mucor hiemalis* IFO-8448, Mucor hiemalis IFO-8449 and Mucor plumbeus CBS 295.63. The yields of 7α,17α,21-trihydroxy-4-pregnene-3,20-dione amounted to 10 mg, 4.5 mg, 7.5 mg, 15 mg and 3 mg respectively.

EXAMPLE 3

A fermentation medium containing 1% glucose and 1% cornsteep liquor was adjusted to pH 6.5. 30 500 ml Erlenmeyer flasks each containing 100 ml of the medium were inoculated with Mucor hiemalis FERM P-3800 and cultivated at 26.5° C. for 2 days on a shaking machine. Thereafter, 20 mg of 11β,17α,21-trihydroxy-4-pregnene-3,20-dione in 0.5 ml of dimethyl sulphoxide were added to each flask and the incubation was continued for 5 days. The culture was filtered and washed with water. The filtrate and washings were extracted with ethyl acetate and the extract was concentrated under reduced pressure. Chromatography on a silica gel column using chloroform/acetone for the elution yielded 58 mg of 7α,17α,21-trihydroxy-4-pregnene-3,11,20-trione of melting point 245.5°–246.5° C.; $\lambda_{max}$ in methanol 238.5 nm ($\epsilon$=10,729).

EXAMPLE 4

100 ml of a medium of the same composition as in Example 3 were inoculated in a 500 ml Erlenmeyer flask with *Mucor hiemalis* FERM P-3800 and incubated at 26.5° C. for 48 hours. Thereafter, 10 mg of 17α,21-dihydroxy-4-pregnene-3,11,20-trione in 0.5 ml of dimethyl sulphoxide were added and the culture was fermented for 98 hours. There were obtained 1.1 mg of 7α,17α,21-trihydroxy-4-pregnene-3,11,20-trione.

EXAMPLE 5

100 ml of the medium of Example 1 were inoculated with Mucor hiemalis FERM P-3800 and shaken at 26.5° C. for 22 hours. The culture was then treated with 50 mg of 17β-hydroxy-4-androsten-3one in 1 ml of dimethyl sulphoxide and incubated for 8 days. There were obtained from the culture filtrate 4.8 mg of 7α,17β-dihydroxy-4-androsten-3-one of melting point 191°–193° C.

We claim:

1. A process for the preparation of 7α-hydroxysteroids of the formula

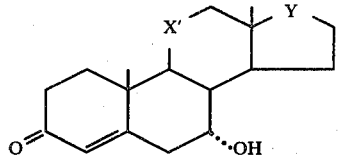

wherein X' is —CH₂— or

and Y is a radical of the formula

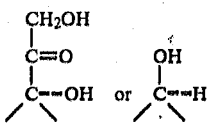

which comprises contacting a 7-unsubstituted steroid of the formula wherein X is —CH₂—, $$-\underset{\underset{\text{CH}}{|}}{\overset{\text{OH}}{|}}-\quad \text{or} \quad -\overset{\overset{\text{O}}{\|}}{\text{C}}-$$

and Y is as above with a microorganism of the genus Mucor in an aqueous culture medium under aerobic conditions.

2. The process of claim 1 wherein the 7-unsubstituted steroid is selected from the group consisting of 17α,21-dihydroxy-4-pregnene-3,20-dione, 11β,17α,21-trihydroxy-4-pregnene-3,20-dione, 17α,21-dihydroxy-4-pregnene-3,11,20-trione and 17β-hydroxy-4-androstene-3-one.

3. The process of claim 1 wherein the microorganism is selected from the group consisting of *Mucor spinescens* IAM-6071, *Mucor circinelloides* ETH-2605, *Mucor hiemalis* IFO-8448, *Mucor hiemalis* IFO-8449, *Mucor plumbeus* CBS 295.63, *Mucor hiemalis* FERM P-No. 3800 and variants thereof.

4. The process of claim 3 wherein the microorganism is selected from the group consisting of *Mucor spinescens* IAM-6071, *Mucor hiemalis* IFO-8448, *Mucor hiemalis* IFO-8449 and *Mucor hiemalis* FERM P-No. 3800.

5. The process of claim 4 wherein the microorganism is *Mucor hiemalis* FERM P-No. 3800.

* * * * *